(12) United States Patent
Lisogurski (10) Patent No.: US 10,993,631 B2
(45) Date of Patent: May 4, 2021

(54) PHYSIOLOGICAL MONITORING METHODS AND SYSTEMS UTILIZING DISTRIBUTED ALGORITHMS

(71) Applicant: Covidien LP, Mansfield, MA (US)

(72) Inventor: Daniel Lisogurski, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 182 days.

(21) Appl. No.: 16/270,488

(22) Filed: Feb. 7, 2019

(65) Prior Publication Data

US 2019/0183363 A1 Jun. 20, 2019

Related U.S. Application Data

(62) Division of application No. 15/047,770, filed on Feb. 19, 2016, now Pat. No. 10,213,121.

(Continued)

(51) Int. Cl.
*A61B 5/02* (2006.01)
*A61B 5/024* (2006.01)
(Continued)

(52) U.S. Cl.
CPC ........ *A61B 5/02416* (2013.01); *A61B 5/1455* (2013.01); *A61B 5/369* (2021.01);
(Continued)

(58) Field of Classification Search
CPC .............. A61B 5/02416; A61B 5/1455; A61B 2560/0443; A61B 5/0476; A61B 5/4821;
(Continued)

(56) References Cited

U.S. PATENT DOCUMENTS 6,298,255 B1 * 10/2001 Cordero ............. A61B 5/04085
600/372
6,708,049 B1  3/2004 Berson et al.
(Continued)

FOREIGN PATENT DOCUMENTS

EP 0171073 A2 2/1986

OTHER PUBLICATIONS

PCT International Search Report and Written Opinion; Application No. PCT/US2016/018585; dated Jul. 11, 2016.

*Primary Examiner* — Amanda K Hulbert
*Assistant Examiner* — Natasha Patel
(74) *Attorney, Agent, or Firm* — Cantor Colburn LLP (57) ABSTRACT

Systems and methods are provided for operating a physiological monitoring system that comprises a distributed algorithm. The physiological monitoring system ma comprise a sensor and a physiological monitor that may be communicatively coupled with the sensor. The sensor may store a first executable code segment and the physiological monitor may store a second executable code segment. The physiological monitor may be configured to receive the first executable code segment and execute the first and second executable code segments to determine at least one physiological parameter of a subject based on physiological signal provided by the sensor. The physiological monitor may be configured to delete or deactivate the first executable code segment. The physiological monitor may also store a configurable algorithm stage that may be configured based on algorithm configuration data received from the sensor.

23 Claims, 5 Drawing Sheets

Related U.S. Application Data (60) Provisional application No. 62/118,406, filed on Feb. 19, 2015.

(51) Int. Cl.
*A61B 5/1455* (2006.01)
*A61B 5/369* (2021.01)
*A61B 5/00* (2006.01)

(52) U.S. Cl.
CPC ........... *A61B 5/4821* (2013.01); *A61B 5/7203* (2013.01); *A61B 5/7264* (2013.01); *A61B 5/7278* (2013.01); *A61B 2560/0443* (2013.01); *A61B 2560/0475* (2013.01); *A61B 2562/08* (2013.01); *A61B 2562/225* (2013.01)

(58) Field of Classification Search
CPC ... A61B 5/7203; A61B 5/7264; A61B 5/7278; A61B 2560/0475; A61B 2562/225
See application file for complete search history.

(56) References Cited

U.S. PATENT DOCUMENTS

| | | |
|---|---|---|
| 6,801,797 B2 | 10/2004 | Mannheimer et al. |
| 7,438,863 B2 | 10/2008 | Evans |
| 7,949,380 B2 | 5/2011 | Fein et al. |
| 8,190,226 B2 | 5/2012 | Berson et al. |
| 8,510,861 B2 | 8/2013 | Eriksson et al. |
| 8,626,256 B2 | 1/2014 | Fein et al. |
| 8,818,474 B2 | 8/2014 | Berson et al. |
| 8,832,461 B2 | 9/2014 | Saroiu et al. |
| 2002/0038081 A1 | 3/2002 | Fein et al. |
| 2005/0037482 A1* | 2/2005 | Braig ............... A61B 5/14546 435/287.1 |
| 2007/0043269 A1 | 2/2007 | Mannheimer et al. |
| 2009/0137885 A1 | 5/2009 | Al-Ali et al. |
| 2011/0196211 A1* | 8/2011 | Al-Ali ............... A61B 5/024 600/300 |
| 2011/0234488 A1 | 9/2011 | Ge et al. |
| 2013/0104288 A1 | 5/2013 | Schlottau et al. |
| 2014/0046152 A1 | 2/2014 | Bechtel et al. |
| 2014/0051942 A1* | 2/2014 | Gillette ............... A61B 5/01 600/301 |
| 2014/0214330 A1 | 7/2014 | Iyer et al. |

\* cited by examiner

PHYSIOLOGICAL MONITORING METHODS AND SYSTEMS UTILIZING DISTRIBUTED ALGORITHMS

CROSS-REFERENCE TO RELATED APPLICATION

This application is a divisional of U.S. application Ser. No. 15/047,770, filed Feb. 19, 2016, entitled "PHYSIOLOGICAL MONITORING METHODS AND SYSTEMS UTILIZING DISTRIBUTED ALGORITHMS", which claims the benefit of the filing date of provisional U.S. Patent Application No. 62/118,406, filed Feb. 19, 2015.

SUMMARY

The present disclosure relates to generating and processing signals in a physiological monitoring system, and more particularly to techniques for modifying or augmenting algorithms stored by a monitor of the physiological system using data stated on a physiological sensor.

The present disclosure is directed towards physiological monitoring systems, such as medical devices that utilize distributed algorithms. In some embodiments, the physiological monitoring system may comprise a sensor configured to store a first executable code segment and generate a photoplethysmography (PPG) signal. The physiological monitoring system may also comprise a physiological monitor that comprises a port, non-transitory memory configured to store a second executable code segment, and at least one processor. The port (e.g., a bi-directional input/output) may be communicatively coupled to the sensor and may be configured to receive the first executable code segment and the PPG signal from the sensor. The at least one processor may be configured to execute the first executable code segment and the second executable code segment to determine at least one physiological parameter of a subject based on the PPG signal. The at least one processor may further be configured to delete the first executable code segment from the monitor, or deactivate the first executable code segment after the sensor becomes communicatively disconnected from the port. By providing part of the executable code on the sensor, new algorithms, software updates, and other improvements may be provided to the monitor without the need for a field update of all installed monitors. Rather, the sensor may carry the most updated code to the monitor for execution during patient monitoring, providing a higher quality calculation of patient parameters than otherwise would be possible without the first executable code segment. Additionally, different types of sensors may have different capabilities, which can be reflected in the executable code segment they carry.

In some embodiments, a physiological sensor may be provided. The physiological sensor may comprise at least one light source configured to generate a light signal, at least one light detector configured to receive the light signal after the light signal has been attenuated by body tissue of a subject, and non-transitory memory (e.g., integrated memory) configured to store a first executable code segment. The physiological sensor may further comprise a port. The port may comprise a bi-directional input/output port, a wireless interface, NFC (near field communication) interface, RFID link, one-wire interface, 12C, SPI, UART, or any other type of a port or communication interface. In some embodiments, the port may also have other capabilities. For example, the port may comprise an output of a photodetector capable of transmitting PPG data. The port may be configured to transmit the light signal to a physiological monitor that is communicatively coupled to the port and to transmit the first executable code segment to the physiological monitor, which is configured to execute the first executable code segment and a second executable code segment stored on the physiological monitor to determine at least one physiological parameter of the subject based on the light signal. The first executable code segment may be deleted or deactivated after the physiological monitor becomes communicatively disconnected from the sensor. In some embodiments, the physiological monitor may become communicatively disconnected from the sensor, for example, when the sensor is physically disconnected form the physiological monitor, or when the sensor is moved out of the wireless range of the physiological monitor.

In some embodiments a physiological monitoring system may be provided. The physiological monitoring system may comprise a sensor that is configured to store algorithm configuration data and generate a photoplethysmographic (PPG) signal. The physiological monitoring system may further comprise a physiological monitor. The physiological monitor may comprise a port that is communicatively coupled to the sensor and is configured to receive the algorithm configuration data and the PPG signal from the sensor. The physiological monitor may comprise non-transitory memory configured to store a sequence of ordered algorithm stages wherein one of the algorithm stages comprises a configurable algorithm stage, the configurable algorithm stage comprising a plurality of alternative executable code segments. The physiological monitor may comprise at least one processor that is configured to select one of the plurality of alternative executable code segments for execution based on the algorithm modification data, and execute each algorithm stage of the sequence of ordered algorithm stages to determine at least one physiological parameter of a subject based On the PPG signal, where the selected alternative executable code segment is executed during the execution of the adjustable algorithm stage.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

The systems and methods described below may be implemented using a physiological monitoring system, such as a pulse oximeter, regional oximeter, a photoplethysmographic (PPG) system, an electroencephalography (EEG) system, a temperature monitoring system, an anesthesia monitoring system, a brain monitoring system, or any other kind of medical monitoring system. In some embodiments, the PPG device may comprise a monitor and a s sot that may be commutatively coupled to the monitor. The sensor may be configured to generate a PPG signal and transmit the signal to the physiological monitor. The physiological monitor may store one or more executable code segments. The physiological monitor may be configured to execute an algorithm for several algorithms) by executing one or more of the executable code segments in a sequence. In some embodiments, the one or more algorithms ma include an algorithm for determining one or more physiological parameters of a subject based on the PPG signal received from the sensor. In some embodiments, it may be desirable for the physiological monitoring system to use algorithms that are specific to a sensor that is currently communicatively coupled to the physiological monitor. For example, the sensor may include specific types of capabilities that other sensors lack. In another example, a sensor may require calibration that is specific to that type of sensor. In yet another example, the sensor may store an update for an algorithm that only works with newer models of sensors. The sensor may be manufactured significantly later than the monitor, and may comprise new executable code segments that may be used by the monitor to operate such newer sensor. Consequently, it may be advantageous to distribute parts of an algorithm between the monitor and the sensor. In some embodiments, parts of the algorithm stored by the sensor may be integrated with parts stored by the monitor when the sensor becomes communicatively coupled to the monitor. In some embodiments, the algorithm stored on the monitor may be modified or configured using data stored on the sensor.

For purposes of this disclosure an "executable code segment" may refer to any distinct executable command or a distinct combination of executable commands. Each executable code segment may be separately addressable. In some embodiments, a processor may be configured to execute the executable code segment. In some embodiments, the executable code segment may comprise one or more executable commands that comprises a function, a software class, a software object, an addressable combination of commands, any other type of a combination of executable commands, or any combination thereof. In some embodiments, the executable code segment may comprise one or more executable commands written in a high-level programming language such as C, C+, BASIC, or any other programming language known in the art. In some embodiments, the executable code segment may comprise one or more executable commands written in an assembly language that is specific to a processor or to a combination of processors (e.g. x86, SPARC, RISC, ARM). In some embodiments, the executable code segment may comprise one or more executable commands written in a scripting language such as Java, PHP, Python, a proprietary scripting language, or any other type of scripting language known in the art. In some embodiments, the executable code segment may comprise script language instructions that may be interpreted by a script interpreter (e.g., Java Virtual Machine or a propriety script interpreter).

For purposes of this disclosure "deactivating" an "executable code segment" may refer to preventing further use of the executable code segment. In some embodiments, a deactivated executable code segment may be marked as inactive or stale, preventing any future use of that executable code segment. In some embodiments, a deactivated executable code segment may be placed into temporary memory and become deleted at a later time when that memory becomes allocated for other purposes. In some embodiments, the future use of the deactivated executable code segment may be prevented by other techniques, such as: configuring other executable code segments not to call or reference the deactivated executable code segment, placing the deactivated executable code segment in an inaccessible memory location, or by any other technique known in the art.

For purposes of this disclosure an "algorithm stage" may refer to an executable command or a combination of executable commands that, when executed, carry out a specific portion of an algorithm. In some embodiments, an algorithm stage may comprise one or more executable code segments. In some embodiments, a sequence of algorithm stages may define an algorithm that is configured for a specific purpose. For example, an algorithm for determining a physiological parameter of a subject may comprise a plurality of algorithm stages (e.g., an algorithm stage for digital signal conditioning, an algorithm stage for signal decimation/interpolation, an algorithm stage for computing a physiological parameter etc.) In some embodiments, the algorithm is executed by executing each of the algorithm stages of the algorithm in a sequence. The sequence of execution may be configured before (e.g., predefined) or during the execution of the algorithm.

For purposes of this disclosure a "configurable algorithm stage" may refer to an algorithm stage that may be modified or configured prior to execution. In some embodiments, configurable algorithm stage may comprise a plurality of alternative executable code segments. In some embodiments, one of the alternative executable code segments may be selected for execution prior to the configurable algorithm stage being executed. The executable code segments that are not, selected, may be not executed when the configurable algorithm stage is executed. In some embodiments, a configurable algorithm stage may comprise a code segment that is modified prior to execution.

For purposes of this disclosure "algorithm configuration data" may refer to any type of a data structure or any other type of data that may be used to configure or modify an algorithm or a configurable algorithm stage. For example, algorithm configuration data may include data that is used to select one of the alternative executable code segments of a configurable algorithm stage for execution. In some embodiments, algorithm configuration data may be used to configure one or more configurable algorithm stages, the sequence of algorithm stages, any other configurable aspect of the algorithm, or any combination thereof. For example, algorithm configuration data may include: data which identifies which executable code segments of the algorithm are to be executed, data that specifies the order of execution of executable code segments, data that specifies hardware capabilities of a device, or any other type of data that may be used to configure an aspect of the algorithm.

In some embodiments, a sensor may be configured to store a first executable code segment. The segment may be transmitted to the physiological monitor when the sensor becomes communicatively coupled to the physiological monitor. In some embodiments, the physiological monitor may then create a complete algorithm that includes the first executable code segment and one or more executable code segments that were stored by the physiological monitor. For example, the complete algorithm may be used to determine one or more physiological parameters (e.g., pulse rate and oxygen saturation) based on the PPG signal. In some embodiments, the sensor may store executable code segments that provide algorithm improvements that are specific to the sensor. In some other embodiments, the sensor may store one or more executable code segments that provide an update that may be specific to that sensor. Once the sensor becomes communicatively disconnected from the physiological monitor, the monitor may delete or deactivate the executable code segment received from the sensor.

In some embodiments, the sensor may be configured to store algorithm configuration data for an algorithm stored on the physiological monitor. The sensor may be configured to transmit the algorithm configuration data to the monitor when the sensor becomes communicatively coupled to the monitor. The monitor may store a sequence of algorithm stages. The monitor may be configured to execute the sequence of algorithm stages to accomplish a certain task, such as determining physiological parameters. Some algorithm stages may be configurable algorithm stages that comprise several alternative executable code segments. For example, some alternative code segments may be specific to certain types of sensors. For each configurable algorithm stage, the monitor may select one of the executable code segments for execution based on the algorithm configuration data received from the sensor. Once the sensor becomes communicatively disconnected from the physiological monitor, the physiological monitor may delete the algorithm configuration data received from the sensor.

As mentioned above, the foregoing techniques may be implemented in an oximeter. An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation invasively by analyzing a blood sample taken from the patient). Pulse oximeters may be included in patient monitoring systems that measure and display various blood flow characteristics including, for example, blood oxygen saturation (e.g., arterial, venous, or both). Such patient monitoring systems, in accordance with the present disclosure, may also measure and display additional or alternative physiological parameters such as pulse rate, respiration rate, respiration effort, blood pressure, hemoglobin concentration (e.g., oxygenated, deoxygenated, and/or total), cardiac output, fluid responsiveness parameters, any other suitable physiological parameters, or any combination thereof.

An oximeter may include at least one light sensor that is placed at a site on a subject. For example, the light sensor may be placed on a fingertip, toe, forehead or earlobe, or in the case of a neonate, across a foot or hand. The light sensor may also be placed at any other suitable location on a subject. The oximeter may use at least one light source to pass light through blood perfused tissue and photoelectrically sense the absorption of the light in the tissue. The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, inverted signal, etc.) may be referred to as the photoplethysmograph (PPG) signal. In addition, the term "PPG signal", as used herein, may also refer to an absorption signal (i.e., representing the amount of light absorbed by the tissue) or any suitable mathematical manipulation thereof. The light intensity or the amount of light absorbed may then be used to calculate any of a number of physiological parameters.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine arterial blood oxygen saturation using two wavelengths of light and a ratio-of-ratios calculation. As another example, the system may determine regional blood oxygen saturation using two wavelengths of light and two detectors located at different distances from the emitters. The system also may identify pulses and determine pulse amplitude, respiration, blood pressure, other suitable parameters, or any combination thereof using any suitable calculation techniques. In some embodiments, the system may use information from external sources (e.g., tabulated data, secondary sensor devices) to determine physiological parameters.

It will be understood that the techniques described herein are not limited to pulse oximeters and may be applied to any suitable physiological monitoring device such as: a single wavelength monitoring device, a regional oximeter, an electroencephalography (EEG) system, a temperature monitoring system, an anesthesia system, a brain monitoring system, or any other kind of medical monitoring system.

Figure 1:
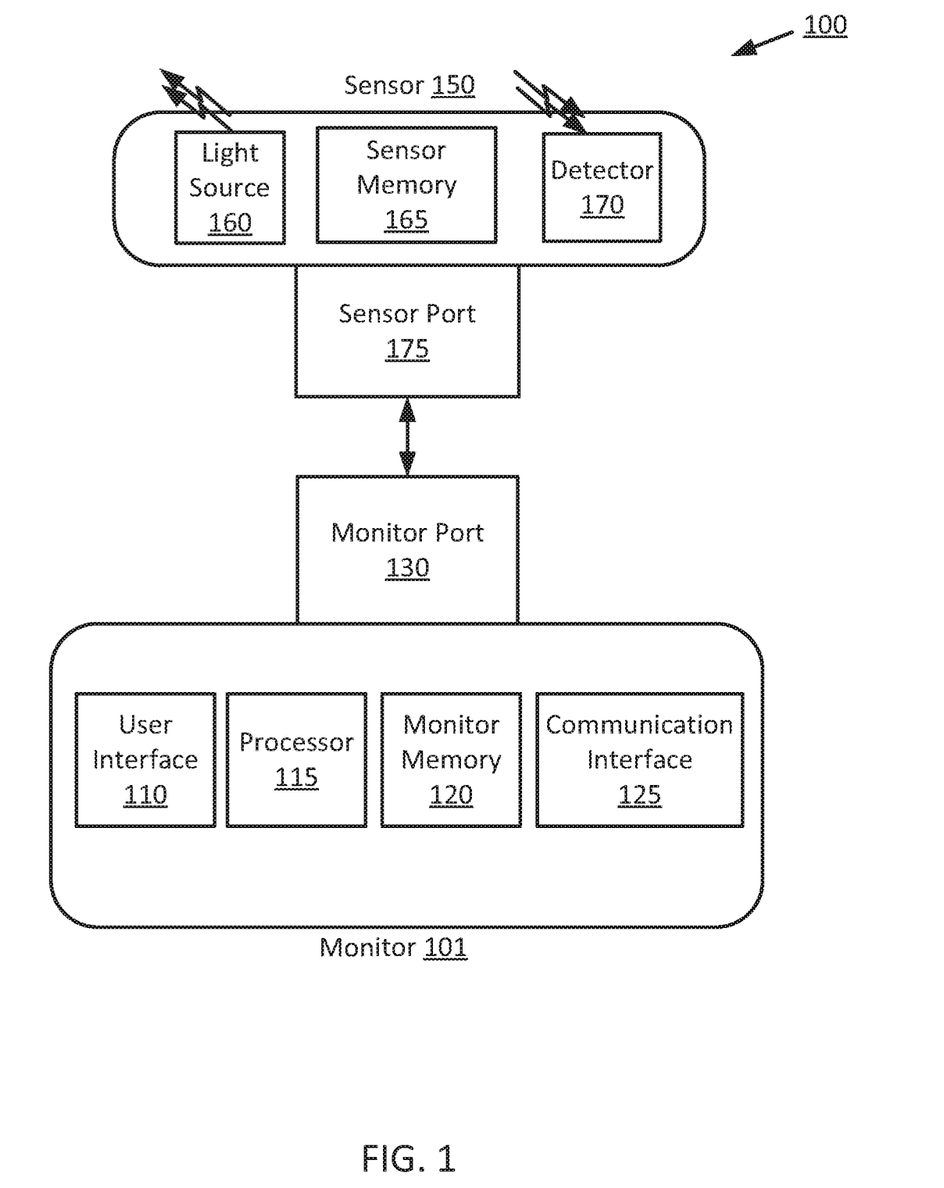
FIG. 1 shows a block diagram of an illustrative physiological monitoring system in accordance with some embodiments of the present disclosure.

FIG. 1 shows a block diagram of illustrative physiological monitoring system 100 in accordance with some embodiments of the present disclosure. System 100 may include a sensor 150 and a monitor 101 for generating and processing sensor signals (e.g., as PPG signal) that may include physiological information relating to a subject. In some embodiments, sensor 150 and monitor 101 may be part of an oximeter. In some embodiments, system 100 may include more than one sensor.

The components of the system 100 are merely illustrative and any suitable components and combinations of components may be used for performing the operations of an oximeter.

Sensor 150 of physiological monitoring system 100 may include light source 160 and detector 170. Light source 160 may be configured to emit photonic signals having one or more wavelengths of light (e.g. red and IR) into a subject's tissue. For example, light source 160 may include a red light, emitting, light source and an IR light emitting light source, e.g. red and IR light emitting diodes (LEDs), for emitting light into the tissue of a subject to generate sensor signals that include physiological information. In one embodiment, the red wavelength may be between about 600 nm and about 750 nm, and the IR wavelength may be between about 800 nm and about 1000 nm. It will be understood that light source 160 may include any number of light sources with any suitable characteristics. In embodiments where array of sensors is used in place of single sensor 150, each sensor may be configured to emit a single wavelength. For example, a first sensor may emit only a red light while a second may emit only an IR light.

It will be understood that, as used herein, the term "light" may refer to energy produced by radiative sources such as electromagnetic radiative sources and may include, for example, any wavelength within the radio, microwave, millimeter wave, infrared, visible, ultraviolet, gamma ray or X-ray spectra. Detector 170 may be chosen to be specifically sensitive to the chosen targeted energy spectrum of light source 160.

In some embodiments, detector 170 may be configured to detect the intensity of light at the red and IR wavelengths. In some embodiments, an array of sensors may be used and each sensor the array may be configured to detect an intensity a single wavelength. In operation, light may enter detector 170 after passing through the subject's tissue. Detector 170 may convert the intensity of the received light into an electrical signal. The light intensity may be directly related to the absorbance and/or reflectance light in the tissue. That is, when more light at a certain wavelength is absorbed or reflected, less light of that wavelength is received from the tissue by detector 170.

After converting the received light to an electrical signal, detector 170 may send the detection signal (e.g., a PPG signal) to monitor 101, here the detection signal may be processed and physiological parameters may be determined. In some embodiments, the detection signal may be preprocessed by sensor 150 before being transmitted to monitor 101. In some embodiments, monitor 101 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In some embodiments, one or more gain settings may be used in analog conditioning to adjust the amplification of the detector signal.

Although only one detector 170 is depicted in FIG. 1, in some embodiments, sensor 150 may include additional detectors located at different distances from the light source 160. In some embodiments, sensor 150 may send the detection signal to monitor 101 using sensor port 175. Sensor port 175 may comprise any kind of wired or wireless connectors suitable for transmitting the detection signal, or any kind of communication of connectors. For example, sensor port 175 may comprise a COM port, Ethernet port, wireless port, a proprietary port, any other communication port, or any combination thereof.

Sensor 150 may include sensor memory 165. Sensor memory 165 may comprise RAM memory, FLASH memory, hard-drive memory, any kind of non-transitory memory, or any combination thereof. Sensor memory 165 may store one or more executable code segments, algorithm configuration data, other types of data or any combination thereof. In some embodiments, sensor 150 may be configured to send the contents of sensor memory 165 to monitor 101. In some embodiments, the contents of sensor memory 165 may be sent using sensor port 175. In some embodiments, the contents of sensor memory 165 may be sent immediately after, or in response to, sensor 150 becoming commutatively coupled to monitor 101. In some embodiments, the contents of sensor memory 165 may be transmitted in response to a request received from monitor 101. The request may specify which contents of sensor memory 165 are to be transmitted.

Sensor 150 may also include additional components not depicted in FIG. 1. For example, sensor 150 may include an internal power source (e.g., a battery) and a wireless transmitter for communicating with monitor 101. As another example, sensor 150 may include additional sensor components such as, for example, a temperature sensor.

In the embodiment shown, monitor 101 includes user interface 110, processor 115, monitor memory 120, and communication interface 125. Monitor 101 may be communicatively coupled to sensor 102 via monitor port 130. Monitor port 130 may comprise any kind of wired connecters, wireless connecters, or any combination of connecters. Wired connecters may use a cable that includes one or more electronic conductors, one or more optical fibers, any other suitable communication components, any suitable insulation or sheathing, or any combination thereof. Monitor port 130 may include a sensor port for mating with a cable. For example, monitor port 130 may comprise a COM port, Ethernet port, wireless port, a proprietary port, any other communication port, or any combination thereof.

Processor 115 may be configured to receive and process the detection signal from sensor 150. Processor 115 may be configured to execute a variety of algorithm stages stored by monitor memory 120 to process the detection signal. Processor 115 may also be configured to execute any software (e.g., algorithm stages comprising executable code segments) stored in monitor memory 120, which may also include an operating system and one or more applications, as part of performing the functions described herein. For example, processor 115 may determine one or more physiological parameters based on the received physiological signals. Processor 115 may include an assembly of analog or digital electronic components. Processor 115 may calculate physiological information. For example, processor 115 may compute one or more of blood oxygen saturation (e.g., arterial, venous, or both), pulse rate, respiration rate, respiration effort, blood pressure, hemoglobin concentration (e.g., oxygenated, deoxygenated, and/or total), cardiac output, fluid responsiveness parameters, any other suitable physiological parameters, or any combination thereof. Processor 115 may perform any suitable signal processing of a signal, such as any suitable scaling, band-pass filtering, adaptive filtering, closed-loop filtering, any other suitable filtering, and/or any combination thereof. Processor 115 may also receive input signals from additional sources not shown. For example, processor 115 may receive an input signal comprising information about treatments provided to the subject from user interface 110. Additional input signals may be used by processor 115 in any of the calculations or operations it performs.

Monitor memory 120 may include any suitable non-transitory computer-readable media capable of storing information that can be interpreted by processor 115. In some embodiments, memory 120 may store calculated values, such as blood oxygen saturation, pulse rate, respiration rate, respiration effort, blood pressure, hemoglobin concentration, cardiac output, and fluid responsiveness parameters, fiducial point locations or characteristics, initialization parameters, adaptive filter parameters, any other calculated values, or any combination thereof, in a memory device for later retrieval. This information may be data or may take the limn of computer-executable instructions, such as software applications, that cause a processor to perform certain functions and/or computer-implemented methods. Computer storage media may include volatile and non-volatile, removable and non-removable media implemented in any method or technology for storage of information such as computer-readable instructions, data structures, program modules, or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Processor 115 may be communicatively coupled with user interface 110 and communication interface 125.

Algorithm stages stored by monitor memory 120 may include a digital conditioning algorithm stage that may be used to perform any suitable digital conditioning of the detector signal. Digital conditioning algorithm stages may include any type of digital filtering of the signal (e.g., low pass, high pass, band pass, notch, or any other suitable filtering), amplifying, performing an operation on the signal, performing any other suitable digital conditioning, or any combination thereof.

Algorithm stages stored by monitor memory 120 may include a decimation/interpolation algorithm stage that may be used to decrease the number of samples in a digital detector signal received from sensor 150. For example, the decimation/interpolation algorithm stage may decrease the number of samples by removing samples from the detector signal or replacing samples a smaller number of samples. The decimation/interpolation algorithm stage may include or be followed by a filtering algorithm stage that may be used to smooth the output signal.

Algorithm stages stored by monitor memory 120 may include an ambient subtraction algorithm stage that may operate on the digital signal. In some embodiments, ambient subtraction algorithm stage may be used to remove dark or ambient contributions to the received signal or signals.

In some embodiments, monitor 101 may be configured to receive a first executable code segment from sensor 150. The first executable code segment may be stored in the sensor memory 165. The sensor 150 may be configured to transmit the first executable code segment to monitor 101 when sensor 150 becomes communicatively coupled to monitor 101. In some embodiments, sensor 150 may be configured to send the first executable code segment via sensor port 175, while monitor 101 may be configured to receive the first executable code segment via monitor port 130. Monitor 101 may also be configured to receive a PPG signal generated by sensor 150.

In some embodiments, monitor memory 120 may be configured to store a second executable code segment. In some embodiments, once monitor 101 receives the first executable code segment, the first executable code segment may also be stored in monitor memory 120. In some embodiments, first and second executable code segments, when combined, may define an algorithm. For example, the first and second executable code segments may define an algorithm that is capable of when executed, determining a physiological parameter of a subject (e.g., pulse rate, oxygen saturation, etc.). In other embodiments, first and second executable code segments may define an algorithm that is capable of accomplishing other tasks, such as: sensor calibration, user communication, host communication, signal conditioning, signal filtering, gain control (including gain control for optimizing signal-to-noise ratio and gain control for patient safety), identifying alarm conditions and generating alarms by integrating multiple physiological factors, optimizing power consumption, generating, a user interface, and generating error codes and informational messages.

In some embodiments, processor 115 may be configured to execute both first and second executable code segments to determine a physiological parameter of a subject based on the PPG signal received from sensor 150. The physiological parameter may then be displayed via user interface 110. In some embodiments, processor 115 may be configured to delete the first executable code segment from monitor memory 120 or deactivate the first executable code segment after sensor 150 becomes communicatively disconnected from monitor 101. In some embodiments, the first executable code segment may be deleted in response to sensor disconnection. Alternatively, the first executable code segment may be deleted after a certain predetermined amount of time has passed after sensor disconnection, or when another sensor becomes coupled to monitor 101.

In some embodiments, monitor memory 120 may store the second executable code segment using permanent memory (e.g., hard disk drive or read only memory), while the first executable code segment is stored using temporary memory (e.g., RAM). In some embodiments, the first executable codes segment may be never stored in full by the temporary memory. Instead, each command of the first executable code may be stored using temporary memory only when necessary for execution of that command. Consequently, the second executable code segment may persist through connection/disconnection of multiple sensors, while the first executable code segment may be deleted due to natural operation of temporary memory. For example, RAM memory may delete the first executable code segment when the first executable code segment is no longer needed and the memory becomes allocated for other purposes. In some embodiments, the temporary memory may delete the first executable code segment when monitor 101 is turned off, restarted, or otherwise reset. In some embodiments, the temporary memory may delete the first executable code segment whenever the temporary memory returns to its native state.

In some embodiments, the second executable code segment may not be, by itself, sufficient to determine a physiological parameter of a subject. In such embodiments, the first executable code segment is necessary for operation of the monitor. In other embodiments, the second executable code segment may be sufficient to determine a physiological parameter of a subject with inferior quality. In these embodiments, the first executable code segment may be used to improve the quality of the physiological parameter determination. In some embodiments, the executable code segment may be used to improve speed, accuracy, margin of error, or any other feature of the physiological parameter determination. In some embodiments, the first executable code segment may include improved mathematic techniques for determining physiological data based on the output of sensor 150. For example, the first executable code segment may provide improvements for pattern matching, noise filtering, operation of a neural net, or any other technique used to determine physiological parameters. In some embodiments, the first executable code segment may include improved techniques for processing the output of sensor 150. For example, the first executable code segment may provide improvements in digital signal conditioning and filtering.

In some embodiments, monitor 101 may be configured to receive algorithm configuration data from sensor 150. The algorithm configuration data be stored in sensor memory 165 and be sent to monitor 101 when sensor 150 becomes communicatively coupled to monitor 101. In some embodiments, sensor 150 may be configured to send the algorithm configuration data via sensor port 175, while monitor 101 may be configured to receive the algorithm configuration data via monitor port 130. Monitor 101 may also be configured to receive the PPG signal generated by sensor 150.

In some embodiments, monitor memory 120 may be configured to store a sequence of ordered algorithm stages.

In some embodiments, the sequence of ordered algorithm stages may define an algorithm that is capable, when executed, of determining a physiological parameter of as subject (e.g., pulse rate, oxygen saturation, etc.). In other embodiments, the sequence of ordered algorithm stages may define an algorithm that is capable for accomplishing other tasks, such as sensor calibration, user communication, or any other task known in the art. Once monitor 101 receives the algorithm configuration data, the algorithm configuration data may be stored in monitor memory 120.

In some embodiments, at least one of the algorithm stages may be a configurable algorithm stage. The configurable algorithm stage may comprise a plurality of alternative executable code segments. In some embodiments, processor 115 may use the algorithm configuration data to select one of the alternative executable code segments for execution based on the algorithm configuration data. Processor 115 may be configured to execute each of the algorithm stages according to the sequence. In some embodiments, when executing the configurable algorithm stage, processor 115 may be configured to only execute the alternative executable code segment that was selected for execution, while other alternative executable code segments may not be executed.

In some embodiments, processor 115 may use the algorithm configuration data to configure the algorithm in other ways. For example, processor 115 may use the algorithm configuration data to reorder the sequence of algorithm stages, modify any of the algorithm stages, create a new algorithm stage, or fetch additional information from external sources using communication interface 125. For example, an algorithm stage for signal conditioning may comprise several alternative executable code segments, each defining a different way of conditioning a signal. The algorithm configuration data may specify which signal conditioning alternative executable code segments should be used when sensor 150 is connected to the monitor 101 in order to improve performance of monitor 101. In another example, monitor 101 may create a new signal conditioning executable code segment based on the algorithm configuration data. In yet another example, monitor 101 may fetch a signal conditioning executable code segment from an external server using a network address specified by the algorithm configuration data.

In some embodiments, processor 115 may use the algorithm configuration data to fetch one or more algorithm stages, alternative code segments or any other data from an external server via the Internet or any other network. In some embodiments, processor 115 may delete the algorithm configuration data from monitor memory 120 after sensor 150 becomes disconnected from monitor 101.

In some embodiments, monitor memory 120 may store the algorithm stages using permanent memory (e.g., flash memory, EEPROM, hard disk drive or read only memory), while the algorithm configuration data is stored using temporary memory (e.g., RAM). Consequently, the algorithm stages may persist through connection/disconnection of multiple sensors, while the algorithm configuration data may be deleted due to natural operation of temporary memory. For example, RAM memory may delete the algorithm configuration data when the algorithm configuration data is no longer needed and the memory is allocated for other purposes. In some embodiments, the temporary memory may delete the algorithm configuration data when the monitor 101 is turned off, restarted, or otherwise reset. In some embodiments, the temporary memory may delete the algorithm configuration data whenever the temporary memory returns to its native state.

In some embodiments, data received by monitor 101 from sensor 150 may be encrypted or signed. In some embodiment, the data may be encrypted with symmetric keys. In another embodiment, the data may be encrypted with asymmetric keys using, for example, private/public key cryptography (e.g., RSA encryption). For example, the data may be encrypted using a public key, and decrypted using a private key stored by monitor memory 120. In some embodiments, the data may be signed using private/public key cryptography, or any other type of cryptography. In some embodiments, the data may be signed using a digital certificate, or a digital certificate chain. Monitor 101 may be configured to verify the digital certificate using a network connection via a commutation interface 125 (e.g., by accessing a website of a certificate issuing authority). In some embodiments, monitor 101 may be configured to reject the data received from sensor 150, if the signature cannot be verified. In some embodiments, the signature may be a part of the executable code segment stored by sensor memory 165, or a part of the algorithm configuration stored by sensor memory 165. In some embodiments, sensor memory 165 may include a checksum data or cyclic redundancy check data that may be used by monitor 101 to verify that information received from the sensor memory has been transmitted correctly. Sensor memory 165 may also include information describing the type of executable code segments (e.g., language of the executable code segments) to ensure that the executable code segments are executed correctly. In some embodiments, sensor memory 165 may have a directory structure which lists available executable code segments and indicates memory locations of the available executable code segments depending on the type of processor 115. For example, if processor 115 is an ARM Cortex-M4 processor, monitor 101 may be provided with a different list of available executable code segments than if processor 115 is an 8051 type processor. In some embodiments, when monitor 101 fails to find executable code segments suitable for its processor type, monitor 101 may not receive any executable code segments from sensor 150.

User interface 110 may include user input, display, and speaker. User interface 110 may include, for example, any suitable device such as one or more medical devices (e.g., a medical monitor that displays various physiological parameters, a medical alarm, or any other suitable medical device that either displays physiological parameters or uses the output of the processor 115 as an input), one more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User interface 110 may include any type of user input device such as a keyboard, a mouse, a touch screen, buttons, switches, a microphone, a joy stick, a touch pad, or any other suitable input device. The inputs received by taste interface 110 can include information about the subject, such as age, weight, height, diagnosis, medications, treatments, and so forth. User interface 110 to may include any type of user output device such as a display, an audio speaker, a haptic device, a printer or any other suitable output device.

In an embodiment, the subject may be a medical patient and user interface 110 may exhibit (e.g., via a monitor) a list of values which may generally apply to the patient, such as, for example, age ranges or medication families, which the user may select using user input. Additionally, user interface 110 may display, for example, an estimate of a subject's blood oxygen saturation, pulse rate information, respiration rate and/or effort information, blood pressure information, hemoglobin concentration information, cardiac output, fluid responsiveness parameters, any other parameters, and any combination thereof. User interface 110 may include any type of display such as a cathode ray tube display, a flat panel display such a liquid crystal display or plasma display, or any other suitable display device. A speaker of user interface 110 may provide an audible sound that may be used in various embodiments, such as for example, sounding an audible alarm in the event that a patient's physiological parameters are not within a predefined normal range.

Communication interface 125 may enable monitor 101 to exchange information with external devices. Communication interface 125 may include any suitable hardware or hardware and software, which may allow monitor 101 to communicate with electronic circuitry, a device, a network, a server or other workstations, a display, or any combination thereof. In some embodiments, communication interface 125 is coupled to sensor port 175 or a digital communications port of an external device. Communication interface 125 may include one or more receivers, transmitters, transceivers, antennas, plug-in connectors, ports, communications buses, communications protocols, device identification protocols, any other suitable hardware and software, or any combination thereof. Communication interface 115 may be configured to allow wired communication, wireless communication, or both. In some embodiments, communication interface 125 may enable monitor 101 to exchange information with external devices such as a ventilator, a capnograph, a trans-thoracic impedance device, a pneumotachometer, any other suitable external devices, and any combination thereof. For example, communication interface 125 may receive respiration information from any of the foregoing external devices, any other suitable devices, or any suitable combination thereof. In some embodiments, communication interface 125 may enable monitor 101 to exchange information with a multi-parameter monitor or a calibration device.

Figure 2:
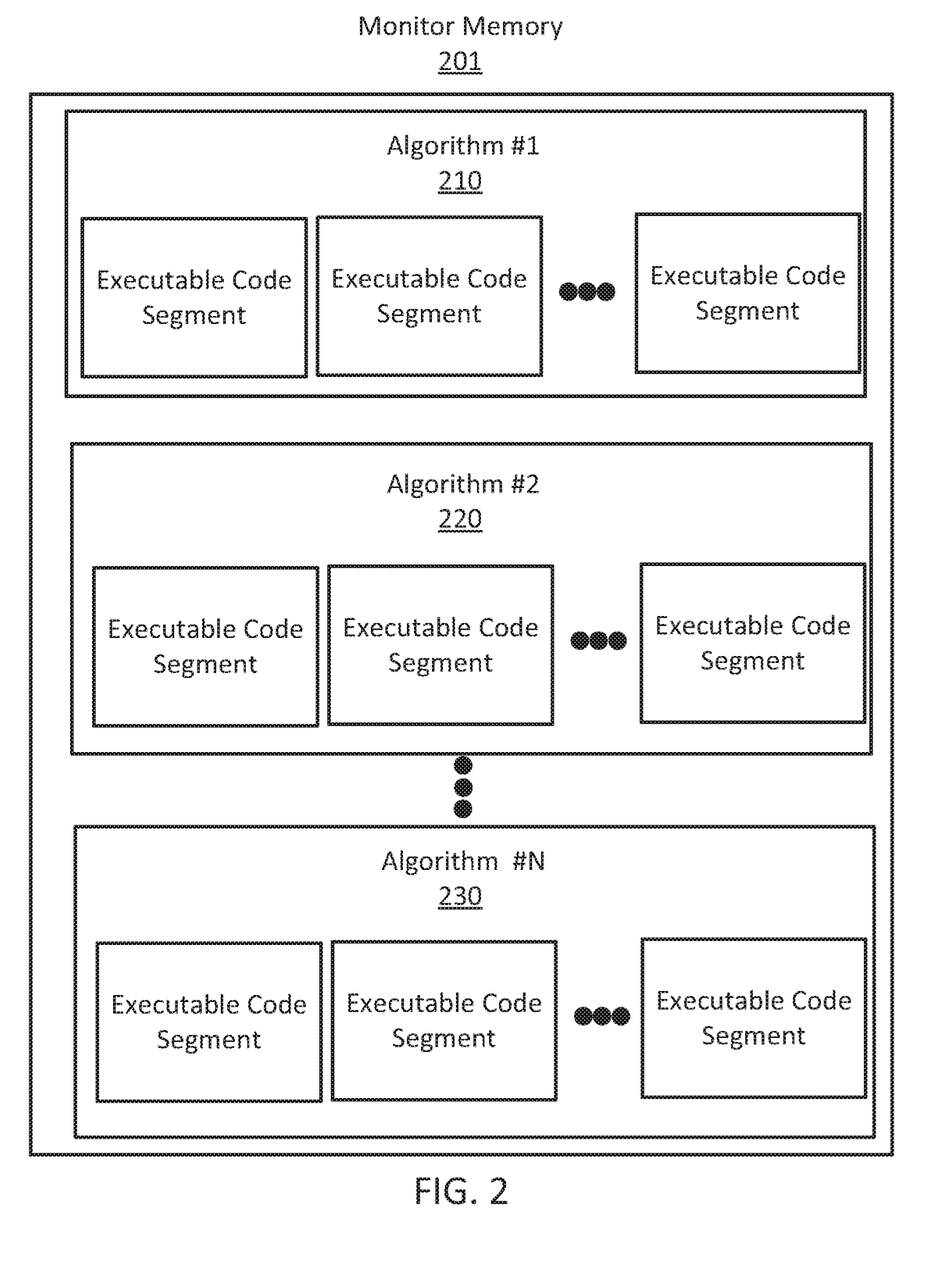
FIG. 2 shows a block diagram of an exempla state of the monitor memory of the physiological monitoring system in accordance with some embodiments of the present disclosure.

FIG. 2 shows a block diagram of an exemplary state of monitor memory 201 of a physiological monitor (e.g., monitor 101 of FIG. 1) in accordance with some embodiments of the present disclosure. In some embodiments, monitor memory 201 may store any number of algorithms. For example, the monitor memory 201 may store several algorithms: algorithm 1 219, algorithm 2 220, . . . , algorithm N 230 (where N is any integer), Algorithms 1-N of FIG. 2 may comprise algorithms for determining physiological parameters of a subject, processing a signal received from a sensor, calibrating the sensor, or for performing any other operation of the monitor.

Each of algorithms 1-N of FIG. 2 may comprise one or more executable code segments. In order to execute one of the algorithms, the processor of the physiological monitoring system may be configured to execute the executable code segments of that algorithm in a specified order. In some embodiments the executable code segments may be organized into algorithm stages.

In some embodiments, Algorithm #1 210 may comprise an algorithm for determining oxygen saturation of a subject. Algorithm #2 210 may comprise a plurality of executable code segments, where each executable code segment is suitable for a particular task. For example, one executable code segment may be suitable for signal conditioning. Another executable code segment may be suitable for subtraction of ambient light. Yet another executable code segment may be suitable for identifying a fiducial point in a PPG signal. In some embodiments, the plurality of executable code segments may comprise all algorithm stages necessary to determine a physiological parameter of a subject. Alternatively, the plurality of executable code segments may lack a certain executable code segment that is needed for determining the physiological parameter of a subject. The executable code segment that is lacking may be received, for example, from a sensor that is communicatively coupled to the monitor.

In some embodiments, Algorithms #1-N of FIG. 2 may include algorithms for determining blood oxygen saturation, pulse rate, blood pressure, breathing information, any other physiological parameter, and any combination thereof. In some embodiments. Algorithms #1-N may include algorithms for calibrating the sensor, operating the user interface, operating the communication interface, or any other purpose that is known in the art.

Figure 3:
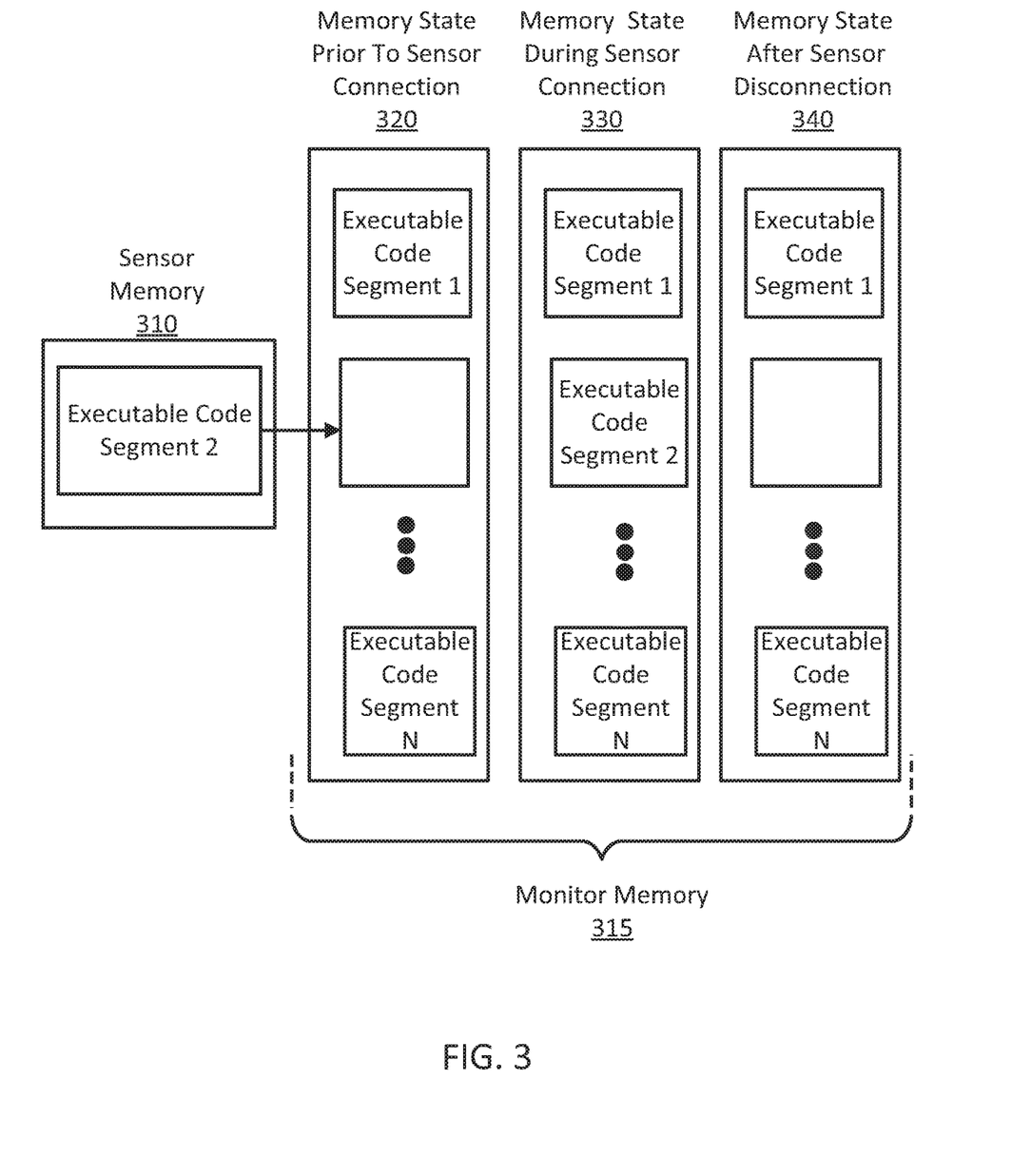
FIG. 3 shows a block diagram of several exemplary states of the monitor memory and sensor memory of the physiological monitoring system in accordance with some embodiments of the present disclosure.

FIG. 3 shows a block diagram of several exemplary memory states 320, 330, and 340 of monitor memory 315 and sensor memory 310 of a physiological monitoring system (e.g., physiological monitoring system 100 of FIG. 1) in accordance with some embodiments of the present disclosure. Memory state 320 illustrates an exemplary state of monitor memory 315 prior to sensor connection. Memory state 330 illustrates an exemplary state of monitor memory 315 during sensor connection. Memory state 340 illustrates an exemplary state of monitor memory 315 after sensor disconnection. Each of memory states 320, 330, and 340 may comprise a plurality of executable code segments. For example, memory state 320 may comprise executable code segments 1-N excluding executable code segment 2.

In some embodiments, sensor memory 310 may comprise an executable code segment (executable code segment 2) that is relevant for determining at least one physiological parameter of a subject. In some embodiments, sensor memory 310 may comprise may comprise other executable code segment, or any other type of data relevant for determining at least one physiological parameter of a subject. In some embodiments, when the mom tor become communicatively coupled to the sensor, the executable code segment 2, that is stored in sensor memory 310, may be transmitted to monitor memory 315. Other executable code segment and other data may also be transmitted to monitor memory 315. In some embodiments, the executable code segment 2 may be transmitted to the monitor memory 315 in response to the sensor becoming, communicatively coupled to the monitor. In some embodiments, the executable code segment 2 may be transmitted to the monitor memory in response to a request from the monitor.

Subsequently, memory state 330, during sensor connection, may contain the executable code segment 2 received from the sensor memory 310. For example, memory state 330 may contain executable code segments 1-N, including executable code segment 2. In some embodiments, memory state 320, prior to sensor connection, may comprise an insufficient amount of executable code segments for determining at least one physiological parameter (or for performing any other task). For example, executable code segment 2, that is necessary for such determination, may be absent from memory state 320. In some embodiment, other necessary executable code segment may also be absent. After the executable code segment 2 is stored by the monitor memory 315, during the sensor connection, memory state 330 may store all executable code segments necessary for determining at least one physiological parameter. In some other embodiments, the memory state 320, prior to sensor connection, may comprise a sufficient amount of executable code segments for determining a physiological parameter with an inferior quality. After the executable code segment 2 is stored by monitor memory 315, during the sensor connection, memory state 330 may store an algorithm that is capable of determining a physiological parameter with an improved quality. For example, the executable code segment 2 may allow the monitor to determine at least one physiological parameter with a higher accuracy, higher speed, higher confidence, any other quality improvement, or any combination thereof. In some embodiments, quality improvement may be achieved due to the executable code segment 2 comprising executable code that is specific to the sensor. For example, executable code segments 1-N (excluding executable code segment 2) may comprise a generic, algorithms suitable for calibrating most sensors that may be coupled to the monitor, while executable code segment 2 may comprise specific executable commands necessary for improved calibration of the sensor that stores executable code segment 2. In some embodiments, the sensor may comprise a less consistent type of an LED light source that may require additional calibration to function properly. Executable code segment 2 may provide one or more executable commands necessary for this additional calibration.

Subsequently, a monitor may become communicatively disconnected from the sensor. In some embodiments, the executable code segment 2 that was received from sensor memory 310 may be deleted from monitor memory 315, after sensor disconnection. In some embodiments, other executable code segments and other types of data that were received from sensor memory 310 may also deleted from monitor memory 315, after sensor disconnection. In some embodiments, the executable code segment 2 that was received from sensor memory 310 may be deactivated, after sensor disconnection. After executable code segment 2 is deleted, memory state 340, after sensor disconnection, may comprise executable code segments 1-N excluding executable code segment 2. In some embodiments, the executable code segment 2 may be deleted from monitor memory 315 in response to the sensor becoming disconnected. In some embodiment, the executable code segment 2 may be deleted from monitor memory 315 after a predetermined amount of time has elapsed after the sensor disconnection. The executable code segment 2 may also be deleted from monitor memory 315 after a different sensor becomes communicatively coupled to the monitor.

Figure 4:
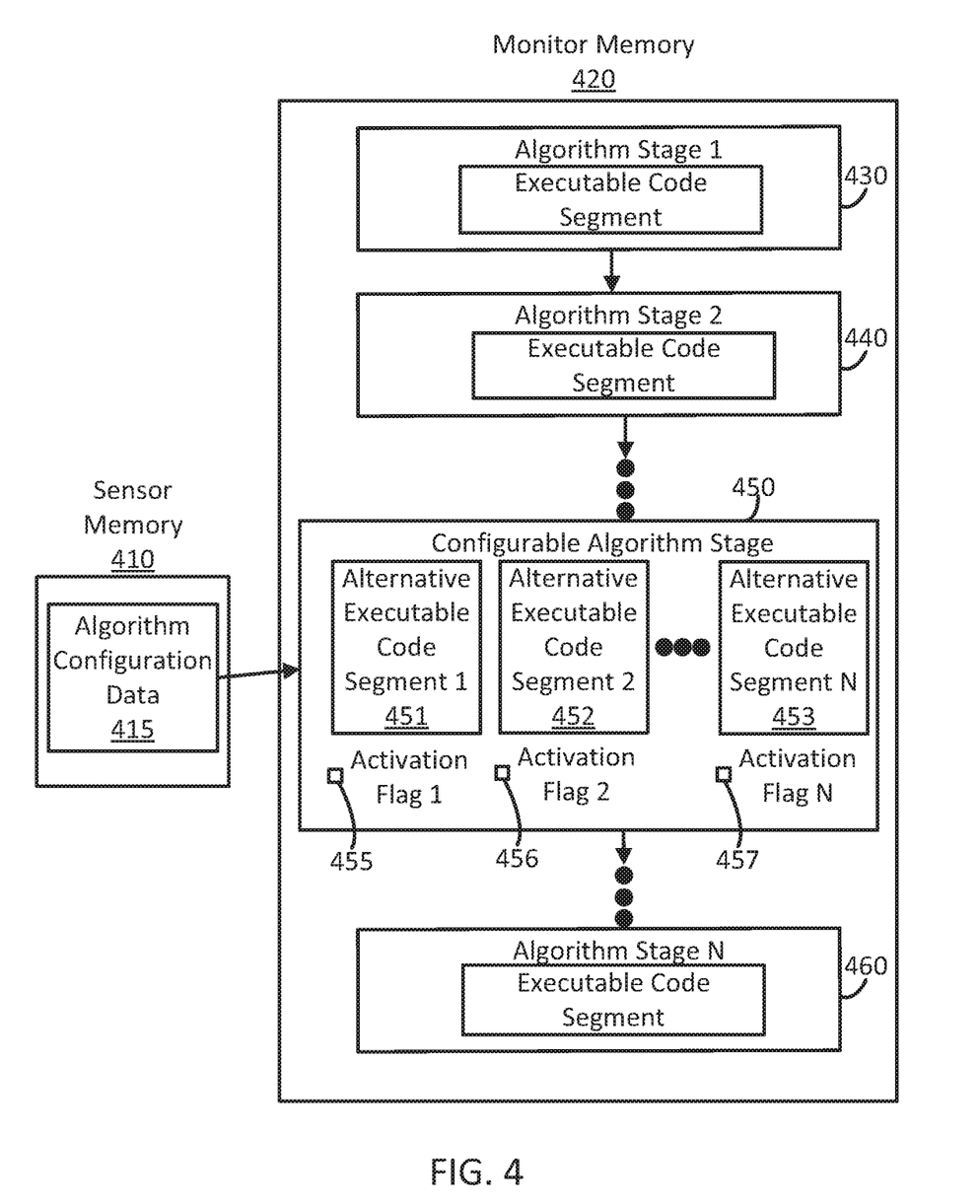
FIG. 4 shows a block diagram of yet another exemplary state of the monitor memory and sensor memory of the physiological monitoring system in accordance with some embodiments of the present disclosure.

FIG. 4 shows a block diagram of monitor memory 420 and sensor memory 410 of a physiological monitoring system (e.g., physiological monitoring system 100 of FIG. 1) in accordance with some embodiments of the present disclosure. In some embodiments, monitor memory 420 may store a sequence of algorithm stages: algorithm stage 1 430, algorithm stage 2 440, configurable algorithm stage 450, . . . , and algorithm stage N 460, where N is any integer. In some embodiments monitor memory 420 may also store more than one configurable algorithm stage. In some embodiments, monitor memory 420 may also store other sequences of algorithm stages. In some embodiments, the sequence of algorithm stages 430, 440, 450, and 460 may be executed in a predetermined order to determine a physiological parameter of subject (or to accomplish any other task). In some embodiments, each of the algorithm stages 430, 440, 450, and 460 may comprise one or more executable code segments.

In some embodiments, algorithm stage 450 may be a configurable algorithm stage. For example, algorithm stage 450 may comprise several executable code segments including: executable code segment 1 451, executable code segment 2 452, executable code segment N 453, where N is any integer. In some embodiments, one of the alternative executable code segments 1-N of FIG. 4 may be selected for execution, before the algorithm stage 450 is executed. In some embodiments, each of the alternative executable code segments 1-N may have an associated activation flag 455, 456, and 457. For example, alternative executable code segments 451 may have an associated activation flag 455. In some embodiments, each of the activation flags 1-N may comprise a single memory bit, where the bit being set to "1" indicates that the activation flag is active, and where the bit being set to "0" indicates that the activation flag is inactive. However, any other activation flag known in the art may also be used. In some embodiments, when configurable algorithm stage 450 is executed, only alternative executable code segments that have an active activation flag, are executed. For example, only executable code segment 451 may be executed if activation flag 455 is active, while all other activation flags are inactive. In some embodiments, only one of the alternative executable code segments 1-N of FIG. 4 may have an active activation flag. Alternatively, several of the alternative executable code segments 1-N may have active activation flags.

In some embodiments, the monitor may set the status of activation flags 1-N of FIG. 4 based on algorithm configuration data 415 received from sensor memory 410. For example algorithm configuration data 415 may indicate which of activation flags 1-N should be active and inactive. In some embodiment, algorithm configuration data 415 may provide data that would allow the monitor to determine which of activation flags 1-N should be active and inactive in another way. For example, algorithm configuration data 415 may identify the model number the sensor, and the monitor may use a look-up table to determine how activation flags 1-N of FIG. 4 should be set. In some embodiment, algorithm configuration data 415 may provide data that would allow the monitor to configure all configurable algorithm stages stored by monitor memory 420.

In some embodiments, the monitor may delete algorithm configuration data 415 after the sensor become communicatively disconnected form the monitor. In some embodiments, the monitor may delete or reset activation flags 1-N of FIG. 4 after the sensor become communicatively disconnected form the monitor. All activation flags 1-N may also be reset after the sensor become communicatively disconnected form the monitor.

Figure 5:
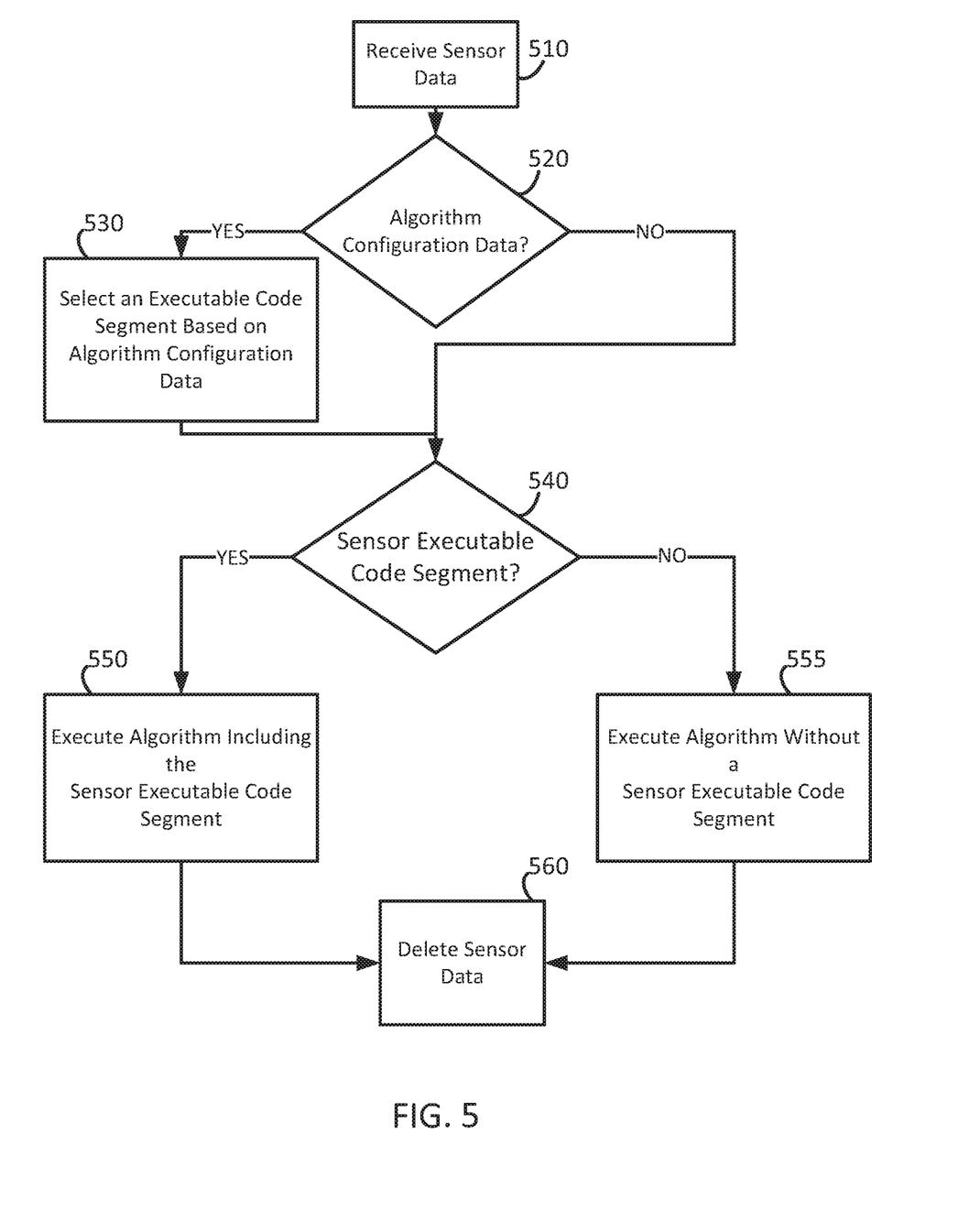
FIG. 5 shows an illustrative flow diagram including steps for creating and executing an algorithm in accordance with some embodiments of the present disclosure.

FIG. 5 shows an illustrative flow diagram including steps for creating and executing an algorithm in accordance with some embodiments of the present disclosure. The steps of FIG. 5 may be carried out by a component of a physiological monitoring system (e.g., system 100 of FIG. 1).

Step 510 may include the physiological monitoring system receiving sensor data from a sensor. The data may be received via a communication port. In some embodiments, the physiological monitoring system may also receive a physiological signal (e.g., a PPG signal) from the sensor. The algorithm sensor data may be received in response to the sensor becoming commutatively coupled to the physiological monitoring system.

Step 520 may include the physiological monitoring system determining if the sensor data comprises algorithm configuration data. In some embodiments, the sensor data may explicitly identify algorithm configuration data. Alternatively, the physiological monitoring system may expect algorithm configuration data by certain features. For example, algorithm configuration data may contain a signature that may be used by the physiological monitoring system to identify algorithm configuration data. If the algorithm configuration data is identified, the physiological monitoring, system may perform step 530, otherwise the physiological monitoring system may proceed to step 540 skipping step 530.

Step 530 may include the physiological monitoring system configuring an algorithm based on the received algorithm configuration data. In some embodiments, the algorithm may be executable to determine at least one physiological parameter of a subject based on a physiological signal received from the sensor. In some embodiments, the algorithm may comprise a configurable algorithm stage that comprises a plurality of alternative executable code segments. The physiological monitoring system may configure the configurable algorithm stage by selecting one of the alternative executable code segments for execution based on the algorithm configuration data. In some embodiments, the alternative executable code segments that were not selected for execution will be not be executed when the algorithm is executed at steps 550 or 555. In some embodiments, the algorithm may be configured based on the algorithm configuration data in other ways known in the art.

Step 540 may include the physiological monitoring system determining if the sensor data comprises a sensor executable code segment. In some embodiments, the sensor executable code segment may be necessary for the algorithm to determine a physiological parameter of the subject. Alternatively, the sensor executable code segment may increase the quality of the physiological parameter algorithm. If an appropriate sensor executable code segment is identified, the physiological monitoring system may execute step 550, alternatively step 555 may be executed.

Step 550 may include the physiological monitoring system executing the algorithm that includes executable code segments that were stored by the physiological monitoring system prior to the sensor becoming coupled to the monitor, and the sensor executable code segment. The algorithm may be used to determine a physiological parameter of the subject. The physiological parameter may be displayed via a user interface. If algorithm configuration data was received, the algorithm executed by the physiological monitoring system at step 550 may include the alternative executable code segment selected at step 530. Alternatively, if algorithm configuration data was not received, the algorithm may be executed without an alternative executable code segment being selected step 530. For example, the algorithm executed at step 550 may not have any alternative executable code segments, or the algorithm may include a default alternative executable code segment.

Step 555 may include the physiological monitoring system executing the algorithm that includes executable code segments stored by the physiological monitoring system prior to the sensor becoming coupled to the monitor and does not include a sensor executable code segment. The algorithm may determine a physiological parameter of the subject, such as heart rate or oxygen saturation. Similar to step 550, the physiological parameter may be displayed via a user interface. If algorithm configuration data was received, the algorithm executed by the physiological monitoring system at step 555 may include the alternative executable code segment selected at step 530. Alternatively, if algorithm configuration data was not received, the algorithm may be executed without an alternative executable code segment being selected step 530. For example, the algorithm executed at step 555 may not have any alternative executable code segments, or the algorithm may include a default alternative executable code segment.

Step 560 may include the physiological monitoring system deleting the sensor data. In some embodiments, the data may be deleted or deactivated after the sensor becomes communicatively disconnected from the physiological monitoring system. For example, the sensor data may be deleted after a predetermined amount of time has passed after the sensor is disconnected. Alternatively, the sensor data may be deleted in response to the sensor becoming disconnected or after another sensor is connected to the physiological monitoring system.

It will be understood that algorithm configuration data received at step 510 may also be used to configure one or more other configurable algorithm stages of the same algorithm or of other algorithms stored by the monitor. It will be understood that data received at step 510 may also comprise one or more other sensor executable code segments that may be incorporated into the same algorithm or into other algorithms stored by the monitor. It will be understood that in some embodiments, steps 510-540 may be performed several times, for example, to configure multiple configurable algorithm stages, and to receive multiple executable code segments. In some embodiments, at step 550, the monitor may execute an algorithm that includes multiple sensor executable code segments. In some embodiments, at step 550 or step 555, the monitor may execute an algorithm that includes multiple configurable algorithm stages. It will be understood that some of the steps of FIG. 5 are optional. For example, in embodiments that do not use algorithm configuration data, steps 520 and 530 may be omitted. As another example, in embodiments that do not use a sensor executable code segment, steps 540 and 550 may be omitted.

It will be understood that the aforementioned techniques are not limited to PPG systems, and may be applied to any suitable signal processing in any suitable system. For example, the techniques may be applied to electrical signals additionally or alternatively to applying it to optical signals. In another example, the techniques may be applied additionally or alternatively to respiration signals.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A physiological monitoring system, comprising:
 a sensor configured to:
   store algorithm configuration data; and
   generate a photoplethysmographic (PPG) signal; and
 a physiological monitor comprising:
   a port communicatively coupled to the sensor, the port being configured to: receive the algorithm configuration data from the sensor; and receive the PPG signal from the sensor;
   non-transitory memory configured to store a sequence of ordered algorithm stages, wherein one of the sequence of the ordered algorithm stages comprises a configurable algorithm stage, the configurable algorithm stage comprising at least one of a plurality of alternative executable code segments; and at least one processor configured to:
- select an alternative executable code segment of the plurality of alternative executable code segments to be executed based on the algorithm configuration data; and
- execute each algorithm stage of the sequence of ordered algorithm stages to determine at least one physiological parameter of a subject based on the PPG signal, wherein the selected alternative executable code segment is executed during the execution of the configurable algorithm stage;
- wherein the stored executable code segments are operable without the algorithm configuration data; and
- wherein the stored executable code segments are maintained in the non-transitory memory of the physiological monitor subsequent to disconnection of the sensor from the port.

2. The physiological monitoring system of claim 1, wherein at least one unselected alternative executable code segment of the plurality of alternative executable code segments is not executed during the execution of the configurable algorithm stage.

3. The physiological monitoring system of claim 1, wherein the at least one processor is configured to delete the algorithm configuration data after the sensor becomes communicatively disconnected from the physiological monitor.

4. The physiological monitoring system of claim 3, wherein the at least one processor is configured to delete the algorithm configuration data or deactivate the selected alternative executable code segment in response to the sensor becoming communicatively disconnected from the physiological monitor.

5. The physiological monitoring system of claim 4, wherein the at least one processor is configured to delete the algorithm configuration data or deactivate the selected alternative executable code segment after a predetermined amount of time has elapsed after the sensor becomes communicatively disconnected from the physiological monitor.

6. The physiological monitoring system of claim 1, wherein the algorithm configuration data is encrypted and wherein the at least one processor is configured to decrypt the algorithm configuration data.

7. The physiological monitoring system of claim 1, wherein the at least one processor is configured to delete the algorithm configuration data in response to the sensor becoming communicatively disconnected from the port or in response to a second sensor becoming communicatively coupled to the port.

8. A physiological monitor, comprising:

a port communicatively coupled to a sensor, the port being configured to:
- receive algorithm configuration data and an executable code segment from the sensor; and
- receive a photoplethysmographic (PPG) signal of a subject from the sensor; non-transitory memory configured to store a sequence of ordered algorithm stages, wherein the sequence of the ordered algorithm stages comprises a configurable algorithm stage, the configurable algorithm stage comprising at least one of a plurality of alternative executable code segments; and at least one processor configured to:
- select an alternative executable code segment of the plurality of alternative executable code segments to be executed with the received executable code segment based on the algorithm configuration data; and
- execute the received executable code segment and each algorithm stage of the sequence of ordered algorithm stages to determine at least one physiological parameter based on the PPG signal, wherein the selected alternative executable code segment is executed during execution of the configurable algorithm stage;
- wherein the stored executable code segments are operable without the algorithm configuration data; and
- wherein the stored executable code segments are maintained in the non-transitory memory of the physiological monitor subsequent to disconnection of the sensor from the port.

9. The physiological monitor of claim 8, wherein the at least one processor is configured to determine the order of execution of the executable code segment and the sequence of ordered algorithm stages based on the algorithm configuration data.

10. The physiological monitor of claim 8, wherein the received executable code segment is executed before the sequence of ordered algorithm stages to determine the physiological parameter.

11. The physiological monitor of claim 8, wherein the at least one processor is configured to delete the algorithm configuration data, the received executable code segment, or both, from the physiological monitor after the PPG sensor becomes communicatively disconnected from the port.

12. The physiological monitor of claim 8, wherein the algorithm configuration data, the received executable code segment, or both, are encrypted, and wherein the at least one processor is configured to decrypt the algorithm configuration data, the received executable code segment, or both.

13. The physiological monitor of claim 8, wherein execution of the received executable code segment and the sequence of ordered algorithm stages results in a higher quality determination of the at least one physiological parameter than execution of the sequence of ordered algorithm stages without the executable code segment.

14. The physiological monitor of claim 8, wherein the sequence of ordered algorithm stages are operable without the received executable code segment.

15. The physiological monitor of claim 8, wherein the at least one processor is configured to delete the algorithm configuration data in response to the sensor becoming communicatively disconnected from the port or in response to a second sensor becoming communicatively coupled to the port.

16. A method of monitoring a subject, the method comprising:

receiving, by a physiological monitor, a photoplethysmographic (PPG) signal and algorithm configuration data from a PPG sensor, wherein the physiological monitor comprises non-transitory memory that stores a sequence of ordered algorithm stages, wherein the sequence of the ordered algorithm stages comprises a configurable algorithm stage, the configurable algorithm stage comprising at least one of a plurality of alternative executable code segments;

selecting, by the physiological monitor, an alternative executable code segment of the plurality of alternative executable code segments to be executed based on the algorithm configuration data; and executing, by the physiological monitor, each algorithm stage of the sequence of ordered algorithm stages to determine at least one physiological parameter of a subject based on the PPG signal, wherein the selected alternative executable code segment is executed during the execution of the configurable algorithm stage;

wherein the stored executable code segments are operable without the algorithm configuration data; and wherein the stored executable code segments are maintained in the non-transitory memory of the physiological monitor subsequent to disconnection of the sensor from the port.

17. The method of claim 16, wherein an unselected alternative executable code segment of the plurality of alternative executable code segments is not executed during the execution of the configurable algorithm stage.

18. The method of claim 17, wherein the physiological monitor is configured to determine a different physiological parameter based on the PPG signal upon execution of the unselected alternative executable code segment during execution of the configurable algorithm stage than the at least one physiological parameter determined upon execution of the selected alternative executable code segment during execution of the configurable algorithm stage.

19. The method of claim 16, comprising storing, by the physiological monitor, the algorithm configuration data in temporary memory of the physiological monitor.

20. The method of claim 16, comprising deleting, by the physiological monitor, the algorithm configuration data after selecting the alternative executable code segment.

21. The method of claim 16, wherein the plurality of alternative code segments comprises a default alternative executable code segment, and wherein the sequence of ordered algorithm stages is operable using the default alternative executable code segment without the selected alternative executable code segment.

22. The method of claim 16, wherein the sequence of ordered algorithm stages comprises a digital conditioning algorithm stage, a decimation algorithm stage, an interpolation algorithm stage, a filtering algorithm stage, or an ambient subtraction algorithm stage.

23. The method of claim 16, further comprising deleting the algorithm configuration data in response to the sensor becoming communicatively disconnected from the port or in response to a second sensor becoming communicatively coupled to the port.

* * * * *